(12) United States Patent
McElroy

(10) Patent No.: US 8,470,736 B2
(45) Date of Patent: Jun. 25, 2013

(54) TURFGRASS QUALITY

(75) Inventor: Scott McElroy, Auburn, AL (US)

(73) Assignee: Syngenta Crop Protection, LLC, Greensboro, NC (US)

( * ) Notice: Subject to any disclaimer, the term of this patent is extended or adjusted under 35 U.S.C. 154(b) by 0 days.

(21) Appl. No.: 13/132,823

(22) PCT Filed: Dec. 1, 2009

(86) PCT No.: PCT/EP2009/008549
§ 371 (c)(1),
(2), (4) Date: Aug. 16, 2011

(87) PCT Pub. No.: WO2010/063446
PCT Pub. Date: Jun. 10, 2010

(65) Prior Publication Data
US 2011/0306497 A1     Dec. 15, 2011

Related U.S. Application Data

(60) Provisional application No. 61/120,069, filed on Dec. 5, 2008.

(51) Int. Cl.
*A01N 25/26* (2006.01)
*A01N 43/00* (2006.01)
*A01N 37/10* (2006.01)

(52) U.S. Cl.
USPC .......................... 504/100; 504/139; 504/144

(58) Field of Classification Search
None
See application file for complete search history.

(56) References Cited

U.S. PATENT DOCUMENTS

| 6,114,284 A | * | 9/2000 | Fujisawa et al. | 504/140 |
| 2005/0032648 A1 | * | 2/2005 | Cooper et al. | 504/148 |
| 2009/0226496 A1 | * | 9/2009 | Mulqueen et al. | 424/408 |

FOREIGN PATENT DOCUMENTS

| CN | 1379980 | 11/2002 |
| CN | 1379981 | 11/2002 |
| EP | 686343 | 12/1995 |
| WO | 2005/107436 | 11/2005 |
| WO | WO-2005107436 | * 11/2005 |

OTHER PUBLICATIONS

Database WPI Week 200322 Thomson Scientific, London, GB; AN 2003-22519 & CN 1379981, Chengdu Biology Inst, Nov. 20, 2002.
Database WPI Week 200322 Thomson Scientific, London, GB; AN 2003-22518 & CN 1379980, Chengdu Biology Inst, Nov. 20, 2002.
D.R. Rudell and J.P. Mattheis: "Synergism exists between ethylene and methyl jasmonate in artificial light-induced pigment enhancement of "Fuji" apple fruit peel", Postharvest Biology and Technology, vol. 27, No. 1, Jan. 1, 2008, pp. 136-140.
Ueda Junichi et al, "Methyl jasmonate-induced stimulation of chlorophyll formation in the basal part of tulip bulbs kept under natural light conditions", Journal of Fruit and Ornamental Plant Research, vol. 14, 2006, pp. 199-210.

* cited by examiner

*Primary Examiner* — Alton Pryor
(74) *Attorney, Agent, or Firm* — Brian McAlhaney

(57) ABSTRACT

The present invention relates to a method for improving turfgrass quality, by applying to the turfgrass a plant growth regulator and jasmonic acid, or a salt or ester thereof, and to a composition comprising the same.

20 Claims, No Drawings

TURFGRASS QUALITY

This application is a 371 of International Application No. PCT/EP2009/008549 Dec. 1, 2009, which claims priority to U.S. 61/120,069, filed Dec. 5, 2008, the contents of which are incorporated herein by reference.

The present invention relates to a method for improving turfgrass quality, by applying to the turfgrass a plant growth regulator and jasmonic acid or a salt or ester thereof, and to a composition comprising the same.

High quality, healthy turf is essential, for example, for lawns, golf courses, sports areas and adjacent to roads. Accordingly, there exists a need for novel methods to enhance turfgrass quality.

Plant growth regulators are often used to regulate the growth and development of crop plants. For example, plant growth regulators are used to slow the development of a crop (such as oil seed rape) so that it flowers at a desired time, reduce the height of a crop (such as in cereals) so that it is less susceptible to lodging, increase nitrogen efficiency, regulate flowering and fruit set of a crop (such as fruit trees), and slow turfgrass growth rate to reduce mowing frequency.

There are several different classes of plant growth regulator. Known classes include azoles (such as uniconazole, and paclobutrazol), cyclohexane carboxylates (such as trinexapac-ethyl, and prohexadione-calcium), pyrimidinyl carbinols (such as flurprimidol, and ancymidol), quarternary ammoniums (such as chlormequat-chloride, and mepiquat-chloride), and sulphonyl-amino phenyl-acetamides (such as mefluidide).

Plant growth regulators operate by various modes of action. For example, onium-type plant growth retardants such as chlormequat-chloride and mepiquat-chloride, that possess a positively charged ammonium, phosphonium or sulphonium group, function by blocking the synthesis of gibberellin early in the biosynthetic pathway. Growth retardants comprising a nitrogen-containing heterocycle, such as flurprimidol, paclobutrazol and uniconazole-P, act as inhibitors of monooxygenases that catalyse oxidative steps in gibberellin biosynthesis. Structural mimics of 2-oxoglutaric acid, such as the acylcyclohexanediones trinexapac-ethyl and prohexadione-calcium, interfere with the late steps of gibberellin biosynthesis. Other plant growth regulators, such as mefluidide, inhibit cell division and differentiation.

Plant growth regulators are used on turf primarily to slow the vertical growth rate, and therefore reduce mowing frequency.

Jasmonic acid is a plant hormone that acts as a signalling compound to induce the production of phytoalexins that protect against herbivory, fungal invasion, and to induce enzymatic antioxidant activity such as superoxide dismutase and catalases. Jasmonic acid is also thought to regulate plant growth when used at low rates by increasing the total phenolic content of leaves, and therefore inducing free radical buffering capacity and reducing shoot growth.

Various derivatives of jasmonic acid are known. For example, the methyl ester of jasmonic acid (methyl jasmonate, MeJA), methyl (1R,2R)-3-Oxo-2-(2Z)-2-pentenyl-cyclopentaneacetate, has the formula

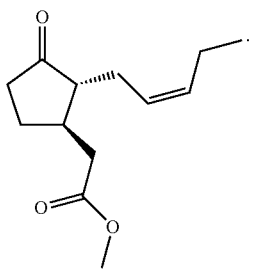

(I)

According to the present invention, there is provided a method for improving turfgrass quality by applying to the turfgrass a plant growth regulator and jasmonic acid, or a salt of ester thereof, wherein the turfgrass is bentgrass.

According to the present invention, there is also provided a method for enhancing the green colour of turfgrass by applying to the turfgrass a plant growth regulator and jasmonic acid or a salt or ester thereof, wherein the turfgrass is bentgrass.

According to the present invention, there is also provided a composition comprising a plant growth regulator and jasmonic acid, or a salt or ester thereof. According to the present invention, there is provided a composition for improving bentgrass quality, comprising a plant growth regulator and jasmonic acid, or a salt or ester thereof. Suitably, the jasmonic acid is in the form of methyl jasmonate.

Improved turfgrass quality and/or colour is particularly pronounced when the compositions of the present invention are applied early in the growing season when turfgrass is growing vigorously. In one embodiment of the present invention, the plant growth regulator and jasmonic acid are applied in the spring.

Reference to the term 'jasmonic acid' herein, includes reference to salts, esters or derivatives of jasmonic acid. In one embodiment of the present invention, the methyl ester of jasmonic acid, methyl jasmonate, is used.

In one embodiment, the plant growth regulator and jasmonic acid are applied to the turfgrass as a composition.

Any plant growth regulator may be used in accordance with the present invention. A complete list of all commercially available plant growth regulators may be obtained from the Pesticide Manual (14$^{th}$ edition, published by the British Crop Protection Council). In one embodiment, the plant growth regulator is selected from the group consisting of trinexapac-ethyl, prohexadione-calcium, paclobutrazol, uniconazole, flurprimidol, mefluidide, mepiquat-chloride, chlormequat-chloride, and a mixture thereof.

Suitably, the plant growth regulator is a gibberellin biosynthesis inhibitor. Suitably, the plant growth regulator is a class A gibberellin biosynthesis inhibitor. Suitably, the plant growth regulator is a class B gibberellin biosynthesis inhibitor. In one embodiment, the plant growth regulator is trinexapac-ethyl or paclobutrazol. In a further embodiment the plant growth regulator is trinexapac-ethyl, prohexadione-calcium or chlormequat-chloride. In one embodiment, the plant growth regulator is trinexapac-ethyl. In one embodiment, the plant growth regulator is prohexadione-calcium. In one embodiment, the plant growth regulator is chlormequat-chloride. In one embodiment, the plant growth regulator is paclobutrazol. In one embodiment, the plant growth regulator is flurprimidol.

Suitably, the jasmonic acid is in the form of methyl jasmonate, and the plant growth regulator is trinexapac-ethyl.

Alternatively, the jasmonic acid is in the form of methyl jasmonate, and the plant growth regulator is paclobutrazol.

If desired, it is possible to use more than one plant growth regulator in combination, in accordance with the present invention. Mixtures of trinexapac-ethyl and paclobutrazol are particularly preferred for use in the present invention with jasmonic acid.

As used herein the term 'turfgrass quality' includes both visual quality of turfgrass and functional quality of turfgrass.

Visual quality of turfgrass relates to the visual appearance, such as density (the number of aerial shoots per unit area), uniformity (for example uniformity of texture, e.g. width of the leaf blades, which can be fine-textured as in red fescue or coarse-textured as in tall fescue) or smoothness (which affects for example the playability of a golf course).

Functional quality of turfgrass relates to, for example, rigidity (resistance of the turfgrass leaves to compression and is related to the wear resistance of a turf), elasticity (tendency of the turfgrass leaves to spring back once a compressing force is removed), resiliency (capacity of a turf to absorb a shock without altering its surface characteristics), ball roll (average distance a ball travels upon being released to a turf surface), yield (measure of clippings removed with mowing), verdure (measure of amount of aerial shoots remaining after mowing), rooting (amount of root growth evident at any one time during the growing season), and recuperative capacity (capacity of turfgrasses to recover from damage caused by disease organisms, insects, traffic and the like).

Improved turfgrass colour relates to enhanced green colour of the grass.

An improvement in the quality of turfgrass can relate to one or more of the visual or functional quality characteristics described above or to any combination of these quality characteristics.

According to the present invention, an "improvement" is a measurable or noticeable increase in a given turfgrass quality characteristic when compared to the same turfgrass quality characteristic produced under the same conditions, but without the application of the subject method. For example, an improvement in the quality characteristics of turfgrass may be a greener or more pleasant, leaf colour of the turfgrass.

The term turfgrass as used herein refers to any grass species from the family Gramineae. For example the grass species may belong to the genera *Agropyron, Agrostis, Axonopus, Bromus, Buchloë, Cynodon, Eremochloa, Festuca, Lolium, Paspalum, Pennisetum, Phleum, Poa, Stenotaphrum* or *Zoysia*. Turfgrass may include more than one grass species.

In a preferred embodiment of the present invention the turfgrass is bentgrass. However, the present invention can be practiced with all turfgrasses, including cool season turfgrass and warm season turfgrass.

Cool season turfgrasses include, for example: Bluegrasses (*Poa* L.), such as Kentucky Bluegrass (*Poa pratensis* L.), Rough Bluegrass (*Poa trivialis* L.), Canada Bluegrass (*Poa compressa* L.) and Annual Bluegrass (*Poa annua* L.); Bentgrasses (*Agrostis* L.), such as Creeping Bentgrass (*Agrostis palustris* Huds.), Colonial Bentgrass (*Agrostis tenius* Sibth.), Velvet Bentgrass (*Agrostis canina* L.) and Redtop (*Agrostis alba* L.); Fescues (*Festuca* L.), such as Creeping Red Fescue (*Festuca rubra* L.), Chewings Fescue (*Festuca rubra* var. commutate Gaud.), Sheep Fescue (*Festuca ovina* L.), Hard Fescue (*Festuca longifolia*), Tall Fescue (*Festuca arundinacea* Schreb.), Meadow Fescue (*Festuca elatior* L.); Ryegrasses (*Lolium* L.), such as Perennial Ryegrass (*Lolium perenne* L.), Annual (Italian) Ryegrass (*Lolium multiflorum* Lam.); Wheatgrasses (*Agropyron* Gaertn.), such as Fairway Wheatgrass (*Agropyron cristatum* (L.) Gaertn.), Western Wheatgrass (*Agropyron smithii* Rydb.); Smooth Brome (*Bromus inermis* Leyss.); and Timothy (*Phleum* L.).

Warm season turfgrasses include, for example Bermudagrasses (*Cynodon* L. C. Rich), Zoysiagrasses (*Zoysia* Willd.), St. Augustinegrass (*Stenotaphrum secundatum* (Walt.) Kuntze), Centipedegrass (*Eremochloa ophiuroides* (Munro.) Hack.), Carpetgrass (*Axonopus* Beauv.), Bahiagrass (*Paspalum notatum* Flugge.), Kikuyugrass (*Pennisetum clandestinum* Hochst. ex Chiov.), Buffalograss (*Buchloe dactyloides* (Nutt.) Engelm.), Centipedegrass (*Eremochloa* spp) and Seashore paspalum (*Paspalum vaginatum* swartz).

To maintain high quality, healthy turfgrass on the intended surface area of ground, such as for example, a golf course, sports field, park area or home lawn, the compositions according to the invention can be applied to the turfgrass once, or more than once, during maintenance of the turfgrass. Suitably, the compositions according to the invention are applied to the turfgrass once, or more than once, during a growing season of the turfgrass.

The plant growth regulator and jasmonic acid of the present invention may be applied either simultaneously or sequentially in any order. If administered sequentially, the components may be administered in any order in a suitable timescale, for example, with no longer than 1 month, no longer than 1 week, or no longer than 24 hours between the time of administering the first component and the time of administering the last component. Suitably, the components are administered within a timescale of a few hours, such as one hour. If the components are administered simultaneously, they may be administered separately or as a tank mix or as a pre-formulated mixture. In one embodiment the mixture or composition of the present invention may be applied to the turfgrass as a seed treatment prior to planting.

When the method of the present invention refers to the application to turfgrass of a co-formulated composition, the composition comprises both plant growth regulator and jasmonic acid. The compounds may be homogeneously mixed together with all other formulation components, and compressed, extruded or granulated to form a solid formulation. Alternatively, the plant growth regulator and jasmonic acid may be mixed together and applied to the surface of a preformed solid formulation as a coating, or in a solvent to be absorbed into the granule. Alternatively the plant growth regulator may be mixed with the other formulation components to form a solid formulation, and jasmonic acid later applied to the surface of said solid formulation, or vice versa.

When the method of the present invention refers to the separate application (either simultaneously or sequentially) to turfgrass of two compositions, one comprising a plant growth regulator, the other comprising jasmonic acid, either or both compositions may be a solid formulation.

The compounds of the present invention may be used in unmodified form, but are generally formulated into compositions using formulation adjuvants, such as carriers, solvents and surface-active substances. The formulations can be in various physical forms, for example dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oil dispersions, suspoemulsions, capsule suspensions, emulsifiable granules, soluble liquids, water-soluble concentrates (with water or a water-miscible organic solvent as carrier), or impregnated polymer films. Such formulations can either be used directly or are diluted prior to use. Diluted formulations can be prepared, for example, with water, liquid fertilizers, micro-nutrients, biological organisms, oil or solvents.

Spreadable formulations, such as granules, are also used for application to turf, especially for application to golf course fairways, hard to spray areas, or other professional turf markets.

The formulations can be prepared, for example, by mixing the plant growth regulator and jasmonic acid (hereinafter referred to as the 'active ingredients') with formulation adjuvants in order to obtain compositions in the form of finely divided solids, granules, solutions, dispersions or emulsions. The active ingredients can also be formulated with other adjuvants, for example finely divided solids, mineral oils, vegetable oils, modified vegetable oils, organic solvents, water, surface-active substances or combinations thereof.

Granule formulations may be distributed by various means, for example by hand. For more effective and even distribution of the desired amount of granular composition a rotary spreader, shaker can or drop spreader may be used. For treating large areas of turfgrass, the granules may be distributed using a mechanical spreader mounted on a tractor or similar device.

Granules may be formulated to provide rapid release of the active ingredients, for example by rapid disintegration upon contact with free moisture. Alternatively, granules may be formulated to provide slow, controlled or delayed release of one or both active ingredients over a prolonged period of time to provide longer-term improvements in turf quality and minimise the need for repeat application.

Granular formulations for use in the present invention include both extrudates and relatively coarse particles. In addition to the active ingredients, generally, the granules can include fillers (also referred to as a carrier), surface active agents (which term can include dispersants and wetting agents) and auxiliary agents such as binders, stabilizers and buffering agents. The filler can be inert, or can serve a biological function, such as acting as a fertilizer. The filler, as well as the other components, preferably should not degrade the active material during the granule preparation or on long term storage or use in the field. Those of skill in the art can readily select appropriate granule components to satisfy these criteria.

Typical carriers for granular formulations include fertiliser, sand, limestone, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, chalk, zeolite, calcite, diatomaceous earth, calcium sulphate and other organic or inorganic materials which absorb, or which can be coated with, a pesticide.

The granular substrate material can be one of the typical carriers mentioned above and/or can be a fertiliser material such as urea/formaldehyde fertilisers, urea, potassium compounds (such as potassium sulphate, nitrate, chloride, oxide, metaphosphate), ammonium compounds (such as ammonium nitrate, sulphate, phosphate), phosphorus compounds (such as phosphoric acid), sulphur, similar plant nutrients and micronutrients and mixtures or combinations thereof. The compounds of the present invention may be homogeneously distributed throughout the granule, spray impregnated or absorbed onto the granule substrate after the granules are formed, or coated onto the surface of the granule.

In general nitrogen based fertilizers are routinely used in turfgrass management to feed grass and stimulate growth. Particularly effective compositions of the present invention are granule compositions having an average particle size of from about 0.5 mm to 2.5 mm, in particular of from 1 mm to 2 mm. These compositions are preferably applied as dry product.

A binder may be used to agglomerate the components of the granules. When present, the binder can be typically used in amounts up to about 20 percent by weight (dry basis) of the granular composition, more typically between about 2 to about 20 percent by weight. The binder binds the ingredients into a granular substrate and maintains particle size during handling. Examples of suitable binders include brewers condensed solubles, lignosulfonate, sodium carbonate lignin, cane molasses, beet syrup, beet molasses, desugared beet molasses, whey, starch, soy solubles with cane molasses or the like, hydrolyzed collagen, amino acid solutions, cellulose derivatives, or cellulose based polymer binders. Other water soluble binders having equivalent properties to, for example, brewer's condensed solubles, can also be used.

Additional auxiliary agents such as surfactants, dispersants, disintegrating agents, wetting agents and the like, can be added where desired to modify the properties of the granules.

Additional components may also be present in the formulations, including surface-active agents such as heavy aromatic naphthas, kerosene and other petroleum fractions, or vegetable oils; and/or stickers such as dextrins, glue or synthetic resins.

Also, the composition of the present invention may optionally include one or more additional pesticides such as insecticides, nematicides, fungicides or herbicides or additional plant growth regulators. This may further improve turfgrass quality through control of insect and nematode pests, fungal diseases, and weeds. Co-formulation of pesticides into the formulation of the present invention has the added benefit of minimising operator time spent applying products to turfgrass, since only a single application may be required to enhance quality and control pests.

Compositions of the present invention may contain from about 0.001% to about 99% by weight active ingredients. Suitably, the composition contains from about 0.001% to about 50% by weight active ingredients. More suitably, the composition contains from about 0.001% to about 10% by weight active ingredients. More suitably, the composition contains from about 0.001% to about 1% by weight active ingredients. If the formulation is in the form of a concentrate, requiring dilution with water before use, it will contain a higher amount of active ingredients than a composition that is ready to use without dilution.

The rate of application of the compounds of the present invention may vary within wide limits and depends upon the nature of the soil, the method of application, the target insect pest to be controlled, the prevailing climatic conditions, and other factors governed by the method of application and the time of application. The compounds of the present invention are generally applied at a rate of 0.001 to 4 kg/ha, especially from 0.005 to 1 kg/ha, in particular of 0.01 to 0.5 kg/ha. Suitably, trinexapac-ethyl is applied at a rate from about 50 to about 100 g ai/ha, and jasmonic acid is applied at a rate from about 100 to about 700 g ai/ha. A particularly preferred rate of trinexapac-ethyl is 96 g ai/ha. A particularly preferred rate of jasmonic acid is 672 g ai/ha.

According to the present invention, there is provided a turfgrass seed treated with a plant growth regulator and jasmonic acid, or a salt or ester thereof, wherein the turfgrass is bentgrass.

According to the present invention, there is also provided the use of a composition comprising a plant growth regulator and jasmonic acid or a salt or ester thereof for improving turfgrass quality and/or enhancing the green colour of turfgrass as described above, wherein the turfgrass is bentgrass.

The compositions according to the invention can be applied to the turfgrass by treating the locus of the turfgrass with a composition according to the invention. For example, the compositions according to the invention can be applied to the soil before or after the seeds of the turfgrass are sown or placed into the soil; or the compositions according to the invention can be applied to a substrate for the growth of turfgrass before or after the seeds of the turfgrass are placed into the substrate; or the compositions according to the invention can be applied to the soil before turfgrass grown on a substrate are placed on top of the soil together with the substrate; or the compositions according to the invention can be applied to turfgrass seed before it is planted.

The following examples further exemplify the present invention. Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the attached claims.

EXAMPLES

Example 1

Compositions comprising methyl jasmonate (as a SL formulation, purchased from Fischer), trinexapac-ethyl (in the form of Primo MAXX®), or both (as a tank mix) were tested at various rates for effects on bentgrass (*Agrostis palustris*) variety Crenshaw. All treatments included the adjuvant NIS, at 0.25% v/v. Assessments of percentage injury to the turfgrass, and turfgrass quality (on a standard scale of 1 to 9) were made at various time intervals after treatment.

TABLE 1

Turfgrass quality

| Rate of TXP (g ai/ha) | Rate of methyl jasmonate (g ai/ha) | Quality (scale: 1 poor to 9 excellent) | | |
|---|---|---|---|---|
| | | 33 DA-A (7 DA-B) | 43 DA-A (17 DA-B) | 56 DA-A (30 DA-B) |
| Untreated control | n/a | n/a | 7.0 | 7.2 | 7.0 |
| Trinexapac-ethyl only | 96 | 0 | 7.2 | 7.4 | 7.0 |
| Methyl jasmonate only | 0 | 168 | 7.1 | 7.2 | 7.0 |
| Methyl jasmonate only | 0 | 336 | 7.0 | 7.2 | 7.0 |
| Methyl jasmonate only | 0 | 670 | 6.9 | 7.0 | 7.0 |
| TXP + methyl jasmonate | 96 | 168 | 7.0 | 7.2 | 7.8 |
| TXP + methyl jasmonate | 96 | 336 | 7.5 | 7.9 | 8.2 |
| TXP + methyl jasmonate | 96 | 670 | 7.5 | 7.9 | 8.2 |

DA-A = days after first application
DA-B = days after second application

The results show that an increase in turfgrass quality was observed when applying mixtures of trinexapac-ethyl with jasmonic acid. The effect is particularly pronounced after a second treatment, resulting in an improvement in turfgrass quality that lasts for at least 56 days after the first treatment.

TABLE 2

Turfgrass colour

| | Rate of TXP (g ai/ha) | Rate of methyl jasmonate (g ai/ha) | Colour (scale: 1 poor to 9 excellent) 43 DA-A (17 DA-B) |
|---|---|---|---|
| Untreated control | n/a | n/a | 7.1 |
| Trinexapac-ethyl only | 96 | 0 | 7.3 |
| Methyl jasmonate only | 0 | 168 | 7.2 |
| Methyl jasmonate only | 0 | 336 | 7.2 |
| Methyl jasmonate only | 0 | 670 | 7.0 |
| TXP + methyl jasmonate | 96 | 168 | 7.2 |
| TXP + methyl jasmonate | 96 | 336 | 8.0 |
| TXP + methyl jasmonate | 96 | 670 | 8.0 |

DA-A = days after first application
DA-B = days after second application

The results show that an improvement in turfgrass green colour was observed when applying mixtures of trinexapac-ethyl with jasmonic acid.

TABLE 3

Injury

| | Rate of TXP (g ai/ha) | Rate of methyl jasmonate (g ai/ha) | Injury (%) | |
|---|---|---|---|---|
| | | | 8 DA-A | 14 DA-A |
| Untreated control | n/a | n/a | 0 | 0 |
| Trinexapac-ethyl only | 96 | 0 | 5 | 7 |
| Methyl jasmonate only | 0 | 168 | 2 | 0 |
| Methyl jasmonate only | 0 | 336 | 0 | 0 |
| Methyl jasmonate only | 0 | 670 | 0 | 0 |
| TXP + methyl jasmonate | 96 | 168 | 2 | 0 |
| TXP + methyl jasmonate | 96 | 336 | 12 | 7 |
| TXP + methyl jasmonate | 96 | 670 | 13 | 10 |

The results show that there does not appear to be a significant difference in turfgrass injury when applying mixtures of trinexapac-ethyl with methyl jasmonate, compared to applying trinexapac-ethyl alone.

Example 2

Compositions comprising methyl jasmonate (purchased from Aldrich), trinexapac-ethyl (in the form of Primo MAXX® 120EC), or both (as a tank mix) were tested at various rates for effects on bentgrass (*Agrostis palustris*) variety A1. Assessments of greenness were made at 5 and 12 days after the second treatment. The results are presented in table 4.

TABLE 4

Colour (Greenness)

|  | Rate of TXP (g ai/ha) | Rate of jasmonic acid (g ai/ha) | Greenness * (5 DA-B) | Greenness ((12 DA-B) |
|---|---|---|---|---|
| Untreated control | n/a | n/a | 0.0 | 0.0 |
| Jasmonic acid only | 0 | 168 | 0.0 | 0.5 |
| Jasmonic acid only | 0 | 336 | 0.0 | 0.0 |
| Jasmonic acid only | 0 | 672 | 0.0 | 0.0 |
| Trinexapac-ethyl only | 57 | 0 | 0.0 | 0.0 |
| TXP + Jasmonic acid | 57 | 168 | 2.0 | 2.0 |
| TXP + Jasmonic acid | 57 | 336 | 1.3 | 1.3 |
| TXP + Jasmonic acid | 57 | 672 | 2.8 | 2.8 |
| Trinexapac-ethyl only | 96 | 0 | 3.5 | 3.5 |
| TXP + Jasmonic acid | 96 | 168 | 3.5 | 3.5 |
| TXP + Jasmonic acid | 96 | 336 | 5.0 | 5.0 |
| TXP + Jasmonic acid | 96 | 672 | 6.8 | 7.0 |

* Greenness assessments were made on a scale of 1-10 by comparison with the untreated control The results show that an improvement in colour was observed when applying mixtures of trinexapac-ethyl and jasmonic acid, especially when each compound is applied at high rates.

Example 3

Compositions comprising methyl jasmonate (as a SL formulation, purchased from Fischer), trinexapac-ethyl (in the form of Primo MAXX®), paclobutrazol (in the form of Trimmit®), or tank mixtures of these products, were tested at various rates for effects on creeping bentgrass (*Agrostis palustris*) variety PennTrio. Table 5 provides a list of treatments made. Assessments of turfgrass quality (on a scale of 0 to 10) and turfgrass colour were made at various time intervals after treatment—the results are presented in Tables 6 and 7.

TABLE 5

Treatments

| Treatment | Description | Product | Rate (fl oz/A) |
|---|---|---|---|
| 1 | Untreated check | None | n/a |
| 2 | TXP only | Primo Maxx ® | 11.0 |
| 3 | TXP + jasmonic acid | Primo Maxx ® | 11.0 |
|  |  | Methyl Jasmonate | 2.42 |
| 4 | TXP + jasmonic acid | Primo Maxx ® | 11.0 |
|  |  | Methyl Jasmonate | 4.84 |
| 5 | TXP + jasmonic acid | Primo Maxx ® | 11.0 |
|  |  | Methyl Jasmonate | 9.7 |
| 6 | PBZ only | Trimmit ® | 16.0 |
| 7 | PBZ + jasmonic acid | Trimmit ® | 16.0 |
|  |  | Methyl Jasmonate | 2.42 |
| 8 | PBZ + jasmonic acid | Trimmit ® | 16.0 |
|  |  | Methyl Jasmonate | 4.84 |
| 9 | PBZ + jasmonic acid | Trimmit ® | 16.0 |
|  |  | Methyl Jasmonate | 9.7 |
| 10 | TXP + PBZ only | Primo Maxx ® | 6.0 |
|  |  | Trimmit ® | 8.0 |
| 11 | TXP + PBZ + jasmonic acid | Primo Maxx ® | 6.0 |
|  |  | Trimmit ® | 8.0 |
|  |  | Methyl Jasmonate | 2.42 |
| 12 | TXP + PBZ + jasmonic acid | Primo Maxx ® | 6.0 |
|  |  | Trimmit ® | 8.0 |
|  |  | Methyl Jasmonate | 4.84 |
| 13 | TXP + PBZ + jasmonic acid | Primo Maxx ® | 6.0 |
|  |  | Trimmit ® | 8.0 |
|  |  | Methyl Jasmonate | 9.7 |

TABLE 6

Turf quality results

| | Turf Quality (Scale 0-10; 0 = poor, 10 = good) | | | | | | | | | | | |
|---|---|---|---|---|---|---|---|---|---|---|---|---|
| Treatment | 8DA-A | 15DA-A | 22DA-A | 32DA-A | 7DA-B | 14DA-B | 22DA-B | 28DA-B | 7DA-C | 14DA-C | 21DA-C | 28DA-C |
| 1 | 8.52 | 8.56 | 8.58 | 8.6 | 8.0 | 8.0 | 8.0 | 8.0 | 7.36 | 7.0 | 6.92 | 7.0 |
| 2 | 8.2 | 8.16 | 8.76 | 8.6 | 9.0 | 8.76 | 8.0 | 8.0 | 9.02 | 8.8 | 9.0 | 9.0 |
| 3 | 8.1 | 8.02 | 8.6 | 8.6 | 9.0 | 9.0 | 8.0 | 8.0 | 9.14 | 9.0 | 9.0 | 9.0 |
| 4 | 8.0 | 8.06 | 8.28 | 8.6 | 9.2 | 9.08 | 8.0 | 8.0 | 9.24 | 9.0 | 9.04 | 9.0 |
| 5 | 8.0 | 8.04 | 8.46 | 8.6 | 9.28 | 9.24 | 8.0 | 8.0 | 9.26 | 9.14 | 9.0 | 9.0 |
| 6 | 8.56 | 8.54 | 8.56 | 8.54 | 8.68 | 8.28 | 8.0 | 8.0 | 8.68 | 8.0 | 7.66 | 8.0 |
| 7 | 8.5 | 8.56 | 8.7 | 8.5 | 8.28 | 8.2 | 8.0 | 8.0 | 8.58 | 8.5 | 7.80 | 8.0 |
| 8 | 8.26 | 8.44 | 8.44 | 8.5 | 8.3 | 8.2 | 8.0 | 8.0 | 8.6 | 8.48 | 8.0 | 8.0 |
| 9 | 8.36 | 8.36 | 8.5 | 8.5 | 8.3 | 8.22 | 8.0 | 8.0 | 9.10 | 8.38 | 7.96 | 8.0 |
| 10 | 8.22 | 8.22 | 8.56 | 8.56 | 8.76 | 8.96 | 9.0 | 8.0 | 9.3 | 9.0 | 9.10 | 9.16 |
| 11 | 8.06 | 8.06 | 8.56 | 8.58 | 8.72 | 9.24 | 9.0 | 8.0 | 9.3 | 9.16 | 9.22 | 9.28 |
| 12 | 8.14 | 8.14 | 8.4 | 8.66 | 8.8 | 9.32 | 9.16 | 8.0 | 9.36 | 9.3 | 9.4 | 9.32 |
| 13 | 7.76 | 7.66 | 8.32 | 8.68 | 8.8 | 9.5 | 9.50 | 8.0 | 9.46 | 9.32 | 9.38 | 9.36 |

DA-A = days after first application; DA-B = days after second application; DA-C = days after third application.

Light shaded cells indicate a numerical improvement in turf quality compared to the applicable PGR only treatment; dark shaded cells indicate a statistically significant improvement in turf quality compared to the applicable PGR only treatment.

The results show that application of trinexapac-ethyl and/or paclobutrazol in combination with methyl jasmonate results in both better turf quality of creeping bentgrass variety PennTrio, than application of the PGRs alone.

TABLE 7

Turf colour results

Turf colour (scale 0-10; 0 = poor, 10 = good)

| Treatment | 8DA-A | 15DA-A | 22DA-A | 32DA-A | 7DA-B | 14DA-B | 22DA-B | 28DA-B | 7DA-C | 14DA-C | 21DA-C |
|---|---|---|---|---|---|---|---|---|---|---|---|
| 1 | 5.0 | 5.0 | 5.0 | 5.0 | 5.0 | 5.0 | 5.0 | 5.0 | 5.0 | 5.0 | 5.0 |
| 2 | 7.0 | 8.0 | 7.3 | 6.0 | 8.0 | 7.1 | 6.0 | 5.6 | 9.0 | 9.2 | 9.0 |
| 3 | 7.1 | 8.0 | 7.18 | 6.0 | 8.12 | 7.52 | 6.0 | 5.8 | 9.2 | 9.42 | 9.0 |
| 4 | 7.28 | 8.0 | 4.34 | 6.0 | 8.3 | 8.0 | 6.0 | 5.6 | 9.2 | 9.48 | 9.18 |
| 5 | 7.44 | 8.0 | 7.18 | 6.0 | 8.3 | 8.0 | 6.0 | 6.0 | 9.24 | 9.48 | 9.16 |
| 6 | 6.0 | 7.0 | 6.2 | 5.2 | 7.5 | 7.1 | 5.0 | 5.32 | 8.0 | 8.26 | 8.0 |
| 7 | 6.3 | 7.0 | 6.0 | 5.0 | 7.88 | 7.0 | 5.0 | 5.58 | 8.3 | 8.3 | 8.0 |
| 8 | 6.14 | 7.0 | 6.1 | 5.0 | 8.0 | 7.32 | 5.0 | 5.7 | 8.24 | 8.42 | 8.0 |
| 9 | 6.26 | 7.0 | 6.28 | 5.0 | 8.0 | 7.3 | 5.0 | 5.72 | 8.24 | 8.4 | 8.0 |
| 10 | 7.5 | 9.0 | 8.0 | 6.2 | 9.0 | 9.0 | 7.0 | 7.0 | 9.22 | 9.0 | 9.28 |
| 11 | 7.68 | 9.0 | 8.0 | 6.6 | 9.16 | 9.0 | 7.32 | 7.0 | 9.36 | 9.1 | 9.52 |
| 12 | 7.5 | 9.0 | 8.0 | 6.6 | 9.3 | 9.0 | 7.65 | 7.0 | 9.38 | 9.22 | 9.54 |
| 13 | 7.6 | 9.0 | 8.0 | 6.8 | 9.3 | 9.0 | 7.64 | 7.0 | 9.48 | 9.22 | 9.36 |

DA-A = days after first application; DA-B = days after second application; DA-C = days after third application.
Light shaded cells indicate a numerical improvement in turf quality compared to the applicable PGR only treatment; dark shaded cells indicate a statistically significant improvement in turf quality compared to the applicable PGR only treatment.

The results show that application of trinexapac-ethyl and/or paclobutrazol in combination with methyl jasmonate results in both better turf colour of creeping bentgrass variety PennTrio, than application of the PGRs alone.

Example 4

A trial was carried out on creeping bentgrass variety L-93, in the same way as described in example 3, using the same treatment list. The results are presented in Tables 8 and 9.

TABLE 8

Turf quality results

Turf Quality (Scale 1-9; 1 = poor, 9 = good)

| Treatment | 14DA-A | 22DA-A | 28DA-A | 6DA-B | 12DA-B | 19DA-B | 28DA-B | 7DA-C | 14DA-C | 21DA-C | 27DA-C | 34DA-C |
|---|---|---|---|---|---|---|---|---|---|---|---|---|
| 1 | 6.0 | 6.7 | 6.6 | 7.1 | 7.5 | 7.4 | 8.0 | 7.6 | 8.0 | 8.0 | 8.0 | 8.6 |
| 2 | 6.0 | 6.9 | 7.2 | 7.9 | 7.7 | 7.4 | 7.6 | 7.7 | 7.8 | 8.8 | 8.6 | 8.0 |
| 3 | 6.0 | 6.6 | 7.1 | 7.6 | 7.6 | 7.6 | 7.7 | 7.4 | 8.0 | 8.6 | 9.0 | 8.2 |
| 4 | 6.0 | 6.7 | 7.0 | 7.5 | 7.5 | 7.5 | 7.6 | 7.6 | 8.0 | 8.8 | 9.0 | 8.8 |
| 5 | 6.0 | 6.9 | 7.6 | 7.6 | 7.9 | 7.5 | 7.9 | 7.5 | 7.8 | 8.6 | 8.8 | 8.6 |
| 6 | 6.0 | 6.6 | 6.9 | 8.0 | 7.5 | 7.7 | 7.9 | 8.0 | 7.7 | 8.0 | 8.6 | 8.4 |
| 7 | 6.0 | 6.5 | 6.9 | 7.2 | 7.5 | 7.3 | 7.7 | 7.6 | 7.7 | 7.7 | 8.2 | 8.6 |
| 8 | 6.0 | 6.9 | 7.1 | 7.7 | 7.2 | 7.6 | 7.9 | 7.4 | 7.9 | 7.7 | 8.4 | 8.6 |
| 9 | 6.0 | 7.0 | 7.0 | 7.6 | 7.6 | 7.6 | 7.6 | 7.8 | 7.6 | 7.7 | 8.2 | 8.8 |
| 10 | 6.0 | 6.9 | 7.5 | 8.0 | 7.7 | 7.6 | 7.8 | 7.8 | 7.8 | 8.6 | 8.2 | 8.4 |
| 11 | 6.0 | 6.9 | 7.3 | 8.2 | 8.0 | 8.0 | 8.0 | 8.1 | 8.2 | 8.6 | 8.8 | 9.0 |
| 12 | 6.0 | 6.8 | 7.0 | 8.0 | 7.5 | 7.8 | 7.7 | 7.8 | 8.0 | 8.2 | 8.4 | 8.6 |
| 13 | 6.0 | 7.2 | 7.4 | 7.9 | 7.8 | 7.5 | 7.8 | 8.0 | 7.8 | 8.2 | 8.2 | 8.4 |

DA-A = days after first application; DA-B = days after second application; DA-C = days after third application.
Shaded cells indicate a numerical improvement in turf quality compared to the applicable PGR only treatment The results show that application of trinexapac-ethyl and/or paclobutrazol in combination with methyl jasmonate results in both better turf quality of creeping bentgrass variety L-93, than application of the PGRs alone.

TABLE 9

Turf colour results

Turf colour (scale 0-10; 0 = poor, 10 = good)

| Treatment | 14DA-A | 22DA-A | 28DA-A | 6DA-B | 12DA-B | 19DA-B | 28DA-B | 7DA-C | 14DA-C | 20DA-C | 27DA-C | 34DA-C |
|---|---|---|---|---|---|---|---|---|---|---|---|---|
| 1 | 6.2 | 6.8 | 6.3 | 6.1 | 6.9 | 7.1 | 7.5 | 6.9 | 7.5 | 7.6 | 7.5 | 7.6 |
| 2 | 6.6 | 6.8 | 7.1 | 7.8 | 7.7 | 8.0 | 7.8 | 7.6 | 8.0 | 8.6 | 8.8 | 8.4 |
| 3 | 7.0 | 7.0 | 7.0 | 8.1 | 7.8 | 8.0 | 7.6 | 7.7 | 8.4 | 9.0 | 9.0 | 8.5 |
| 4 | 7.0 | 6.8 | 6.9 | 7.6 | 8.0 | 8.0 | 7.9 | 7.8 | 8.2 | 9.0 | 8.8 | 8.6 |
| 5 | 6.8 | 7.5 | 7.8 | 7.6 | 7.6 | 7.8 | 7.7 | 7.8 | 8.3 | 9.0 | 8.6 | 8.0 |
| 6 | 6.0 | 6.4 | 6.7 | 7.0 | 7.5 | 7.3 | 7.4 | 7.1 | 7.7 | 7.2 | 7.5 | 7.8 |
| 7 | 6.6 | 6.6 | 6.3 | 6.3 | 6.9 | 7.0 | 7.2 | 6.6 | 7.2 | 7.5 | 7.6 | 8.4 |
| 8 | 7.0 | 6.9 | 6.8 | 6.8 | 7.3 | 7.3 | 7.5 | 7.0 | 7.5 | 7.3 | 7.5 | 8.0 |
| 9 | 6.6 | 6.6 | 6.4 | 7.5 | 7.8 | 7.8 | 7.6 | 7.4 | 7.5 | 7.4 | 7.4 | 8.0 |
| 10 | 6.6 | 6.8 | 7.2 | 7.9 | 7.9 | 7.9 | 7.6 | 7.7 | 7.8 | 8.2 | 8.3 | 8.2 |
| 11 | 6.2 | 6.9 | 7.4 | 7.8 | 7.8 | 7.9 | 7.8 | 7.9 | 8.3 | 8.1 | 8.2 | 8.4 |
| 12 | 6.8 | 6.6 | 7.1 | 7.9 | 7.8 | 7.6 | 7.8 | 7.6 | 7.7 | 8.1 | 7.8 | 8.1 |
| 13 | 6.8 | 6.8 | 7.1 | 7.7 | 7.8 | 7.9 | 7.6 | 7.7 | 7.5 | 8.1 | 8.1 | 8.4 |

DA-A = days after first application; DA-B = days after second application; DA-C = days after third application.
Shaded cells indicate a numerical improvement in turf quality compared to the applicable PGR only treatment The results show that application of trinexapac-ethyl and/or paclobutrazol in combination with methyl jasmonate results in both better turf colour of creeping bentgrass variety L-93, than application of the PGRs alone.

The invention claimed is:

1. A method which improves turfgrass quality comprising applying to the turfgrass a plant growth regulator selected from the group consisting of trinexapac-ethyl, prohexadione-calcium and mixtures thereof and jasmonic acid, or a salt or ester thereof, wherein the turfgrass is bentgrass.

2. A method according to claim 1, wherein the plant growth regulator and jasmonic acid are applied simultaneously.

3. A method according to claim 1, wherein the plant growth regulator and jasmonic acid are applied to the turfgrass separately, in any order.

4. A method according to claim 1, wherein the plant growth regulator and jasmonic acid are applied to turfgrass seed before it is planted.

5. A method according to claim 1, wherein the plant growth regulator and jasmonic acid are applied as a composition.

6. A method according to claim 1, wherein the jasmonic acid is applied in the form of methyl jasmonate.

7. A method according to claim 1, wherein the plant growth regulator is trinexapac-ethyl.

8. A method according to claim 1, wherein the turfgrass is creeping bentgrass.

9. A method according to claim 1, wherein the jasmonic acid is applied in the form of methyl jasmonate.

10. A method which enhances the green colour of turfgrass comprising applying to the turfgrass a plant growth regulator selected from the group consisting of trinexapac-ethyl, prohexadione-calcium, paclobutrazol, uniconazole and mixtures thereof and jasmonic acid or a salt or ester thereof, wherein the turfgrass is bentgrass.

11. A method according to claim 10, wherein the plant growth regulator and jasmonic acid are applied simultaneously.

12. A method according to claim 10, wherein the plant growth regulator and jasmonic acid are applied to the turfgrass separately, in any order.

13. A method according to claim 10, wherein the plant growth regulator and jasmonic acid are applied to turfgrass seed before it is planted.

14. A method according to claim 10, wherein the plant growth regulator and jasmonic acid are applied as a composition.

15. A composition comprising, at an effective application rate to improve turfgrass quality, a plant growth regulator selected from the group consisting of trinexapac-ethyl, prohexadione-calcium and mixtures thereof and jasmonic acid, or a salt or ester thereof.

16. A composition according to claim 15, wherein the jasmonic acid is in the form of methyl jasmonate.

17. A composition according to claim 15, wherein the plant growth regulator is trinexapac-ethyl.

18. A turfgrass seed treated to enhance the green colour of turfgrass, with a plant growth regulator selected from the group consisting of trinexapac-ethyl, prohexadione-calcium, paclobutrazol, uniconazole and mixtures thereof and jasmonic acid, or a salt or ester thereof, wherein the turfgrass is bentgrass.

19. A composition comprising, at an effective application rate to enhance the green colour of turfgrass, a plant growth selected from the group consisting of trinexapac-ethyl, prohexadione-calcium, paclobutrazol, uniconazole and mixtures thereof and jasmonic acid, or a salt or ester thereof.

20. A composition according to claim 19, wherein the jasmonic acid is in the form of methyl jasmonate.

* * * * *